United States Patent
Jamison et al.

(10) Patent No.: US 9,939,553 B2
(45) Date of Patent: Apr. 10, 2018

(54) METHODS AND APPARATUSES FOR DERIVING WELLBORE FLUID SAG FROM THERMAL CONDUCTIVITY MEASUREMENTS

(71) Applicant: Halliburton Energy Services, Inc., Houston, TX (US)

(72) Inventors: Dale E. Jamison, Humble, TX (US); Cato Russell McDaniel, The Woodlands, TX (US); Katerina V. Newman, Houston, TX (US); Xiangnan Ye, Cypress, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 148 days.

(21) Appl. No.: 14/893,541

(22) PCT Filed: Dec. 19, 2014

(86) PCT No.: PCT/US2014/071360
§ 371 (c)(1),
(2) Date: Nov. 24, 2015

(87) PCT Pub. No.: WO2016/099529
PCT Pub. Date: Jun. 23, 2016

(65) Prior Publication Data
US 2016/0356919 A1 Dec. 8, 2016

(51) Int. Cl.
*E21B 43/26* (2006.01)
*G01V 9/00* (2006.01)
(Continued)

(52) U.S. Cl.
CPC ............... *G01V 9/005* (2013.01); *C09K 8/03* (2013.01); *C09K 8/80* (2013.01); *E21B 21/01* (2013.01);
(Continued)

(58) Field of Classification Search
CPC ...... E21B 47/065; E21B 43/267; E21B 21/01; E21B 21/062; C09K 8/80; C09K 8/03;
(Continued)

(56) References Cited

U.S. PATENT DOCUMENTS 5,086,646 A * 2/1992 Jamison ............... E21B 49/005
73/61.63
6,330,826 B1 * 12/2001 Meeten ................. G01N 11/14
73/152.62
(Continued)

FOREIGN PATENT DOCUMENTS

WO 2008118956 A1 10/2008
WO 2016099529 A1 6/2016

OTHER PUBLICATIONS

Omland et al., Detection Techniques Determining Weighting Material Sag in Drilling Fluid and Relationship to Rheology, Annual Transactions of the Nordic Rheology Society, vol. 15, 2007.
(Continued)

*Primary Examiner* — Jennifer H Gay
(74) *Attorney, Agent, or Firm* — McDermott Will & Emery LLP

(57) ABSTRACT

Thermal conductivity measurements of a wellbore fluid may be used to derive the sag of the wellbore fluid (i.e., the inhomogeneity or gradation in particle distribution in the fluid as a result of the particles settling). For example, a method may include measuring a thermal conductivity of a fluid at two or more locations along a height of a vessel containing the fluid that comprises particles dispersed in a base fluid; and calculating a sag of the fluid based on the thermal conductivity at the two or more locations. In some instances, the temperature and pressure of the wellbore fluid may be changed and/or the wellbore fluid may be sheared to investigate their effects on sag.

18 Claims, 7 Drawing Sheets

(51) Int. Cl.
*C09K 8/80* (2006.01)
*E21B 21/00* (2006.01)
*C09K 8/03* (2006.01)
*E21B 21/01* (2006.01)
*E21B 21/06* (2006.01)
*E21B 43/267* (2006.01)
*G01N 11/00* (2006.01)
*C09K 8/50* (2006.01)

(52) U.S. Cl.
CPC .......... *E21B 21/062* (2013.01); *E21B 43/267* (2013.01); *G01N 11/00* (2013.01); *C09K 8/50* (2013.01); *G01N 2011/0093* (2013.01)

(58) Field of Classification Search
CPC .. C09K 8/50; G01N 11/00; G01N 2011/0093; G01V 9/005
See application file for complete search history.

(56) References Cited

U.S. PATENT DOCUMENTS

| | | | | |
|---|---|---|---|---|
| 7,845,212 B1* | 12/2010 | Bi | ................. | G01N 15/04 73/61.63 |
| 2003/0236172 A1* | 12/2003 | Temple | ................. | C09K 8/32 507/100 |
| 2004/0002426 A1* | 1/2004 | Temple | ................. | C09K 8/32 507/100 |
| 2005/0164891 A1* | 7/2005 | Falana | ................. | C09K 8/32 507/103 |
| 2009/0186781 A1* | 7/2009 | Zhang | ................. | C09K 8/032 507/140 |
| 2010/0181070 A1* | 7/2010 | Harris | ................. | C09K 8/04 166/280.1 |
| 2011/0083503 A1* | 4/2011 | Iverson | ................. | G01N 29/024 73/290 V |
| 2011/0130965 A1* | 6/2011 | Slater | ................. | G01N 33/2823 702/9 |
| 2011/0167901 A1* | 7/2011 | Jamison | ................. | G01N 9/00 73/152.18 |
| 2012/0165231 A1* | 6/2012 | Miller | ................. | C09K 8/03 507/143 |
| 2013/0186197 A1 | 7/2013 | Jamison et al. | | |
| 2013/0312511 A1* | 11/2013 | Jamison | ................. | G01N 9/00 73/152.05 |
| 2013/0341008 A1 | 12/2013 | Brady et al. | | |
| 2014/0172305 A1* | 6/2014 | Jamison | ................. | E21B 47/0905 702/9 |
| 2014/0202772 A1* | 7/2014 | Kulkarni | ................. | E21B 21/08 175/65 |
| 2014/0209290 A1* | 7/2014 | Jamison | ................. | E21B 21/01 166/90.1 |
| 2014/0209386 A1* | 7/2014 | Jamison | ................. | C09K 8/032 175/65 |
| 2014/0209387 A1* | 7/2014 | Jamison | ................. | C09K 8/032 175/65 |
| 2014/0209388 A1* | 7/2014 | Jamison | ................. | E21B 21/00 175/65 |
| 2014/0209390 A1* | 7/2014 | Jamison | ................. | C09K 8/032 175/213 |
| 2014/0209391 A1* | 7/2014 | Jamison | ................. | C09K 8/03 175/217 |
| 2014/0209392 A1* | 7/2014 | Jamison | ................. | C09K 8/48 175/217 |
| 2014/0209393 A1* | 7/2014 | Jamison | ................. | E21B 21/00 175/217 |
| 2014/0355645 A1* | 12/2014 | Cheng | ................. | G01N 15/04 374/44 |
| 2015/0354343 A1* | 12/2015 | Wroblewski | ................. | G01N 29/024 73/152.18 |
| 2016/0138395 A1* | 5/2016 | Kulkarni | ................. | E21B 44/00 166/250.01 |
| 2016/0356692 A1* | 12/2016 | Ye | ................. | G01N 21/49 |
| 2016/0356919 A1* | 12/2016 | Jamison | ................. | C09K 8/80 |

OTHER PUBLICATIONS

International Search Report and Written Opinion for PCT/US2014/071360 dated Sep. 25, 2015.
Zamora et al., Improved Wellsite Test for Monitoring Barite Sag, AADE Drilling Fluids Techical Conference, 2004 AADE-04-DF-HO-19,.
PEH: Fluid Mechanics for Drilling, http://petrowiki.org/PEH%3AFluid_Mechanics_for_Drilling, downloaded Nov. 23, 2015.
API Recommended Practice 13D-Rheology and Hydraulics of Oil-Well Drilling Fluids, 2009.

* cited by examiner

METHODS AND APPARATUSES FOR DERIVING WELLBORE FLUID SAG FROM THERMAL CONDUCTIVITY MEASUREMENTS

BACKGROUND

The embodiments described herein relate to sag in wellbore fluids.

Wellbore fluids often include a plurality of particles that impart specific properties (e.g., viscosity, mud weight (or density), and the like) and capabilities (e.g., wellbore strengthening) to the wellbore fluid. It should be understood that the terms "particle" and "particulate," as used in this disclosure, includes all known shapes of materials, including substantially spherical materials, fibrous materials, polygonal materials (such as cubic materials), and combinations thereof.

In drilling fluids, for example, weighting agents (i.e., particles having a specific gravity greater than the base fluid of the drilling fluid) can be used to produce drilling fluids with the desired mud weight (i.e., density), which affects the equivalent circulating density ("ECD") of the drilling fluid. During drilling operations, for example, the ECD is often carefully monitored and controlled relative to the fracture gradient of the subterranean formation. Typically, the ECD during drilling is close to the fracture gradient without exceeding it. When the ECD exceeds the fracture gradient, a fracture may form in the subterranean formation and drilling fluid may be lost into the subterranean formation (often referred to as lost circulation). In another example, lost circulation materials ("LCMs") can be used to strengthen the wellbore and increase the hoop stress around the wellbore, which allows for a higher ECD. The LCMs incorporate into and plug microfractures extending from the wellbore, so as to mitigate fracture propagation and lost circulation.

As used herein, the term "sag" refers to an inhomogeneity or gradation in particle distribution in the fluid as a result of the particles settling (e.g., under the influence of gravity or secondary flow). When sag is observed with weighting agents, the density of the fluid is inhomogeneous or graded.

Oftentimes in a wellbore operation, the circulation of the wellbore fluids through the drill string and wellbore is halted such that the wellbore fluid becomes substantially static in the wellbore (e.g., drill string tripping). In some instances, low shear conditions may be result from slowing circulation or halting circulation while rotating the drill string. As used herein, the term "low shear" refers to a circulation rate with an annular velocity less than about 10 ft/min or a drill string rotation rate of less than 10 rpm. Static or low shear wellbore fluids may allow the particles to settle (i.e., sag). Sag may not occur throughout an entire wellbore, but its occurrence in even a small section of the wellbore can cause well control issues like kicks, lost circulation, stuck pipes, wellbore collapse, and possibly a blowout. For example, if the density of the wellbore fluid, and consequently hydrostatic pressure, are higher than the fracture gradient of the formation, the formation may fracture and cause a lost circulation well control issue. In another example, sag may lead to a portion of the wellbore fluid having a sufficiently high density for a pipe to get stuck therein. Unsticking the pipe can, in some instances, cease the wellbore operation and require expensive and time consuming methods. In yet another example, large density variations in a sagging wellbore fluid may result in wellbore collapse. In another example, the lower density portion of the sagged fluid may, in some instances, readily flow when circulation is resumed or increased and leave the higher density portion of the fluid in place, which is time consuming and expensive to remove. Each of these well control issues and potential remediation are expensive and time consuming.

Sag in wellbore fluids is exacerbated by higher temperatures and deviation in the wellbore. Therefore, the recent strides in extended reach drilling, which have resulted in highly deviated wellbores at greater depths where temperatures can be greater, increase the concern for and possible instances of sag related problems in the oil and gas industry.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

The embodiments described herein relate to sag in wellbore fluids, specifically, methods and apparatuses for deriving the sag of a wellbore fluid from thermal conductivity measurements.

Figure 1:
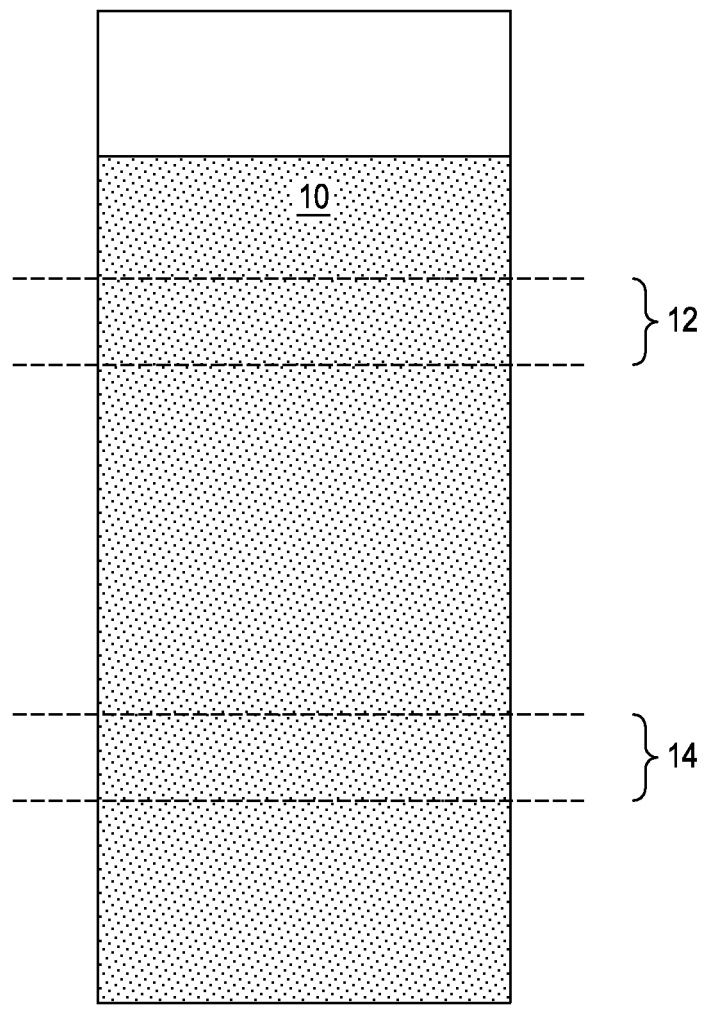
FIG. 1 provides an illustration of portions of a fluid that may be analyzed for calculating sag in the fluid.

Sag may be expressed as a unitless factor according to Equations 1 or 2. As illustrated in FIG. 1, the mass (m) of particles in the fluid 10 or the density ($\rho$) of the fluid 10 is measured for two portions 12,14 of the fluid 10. While the two portions 12,14 are illustrated as being separated by additional fluid 10, the two portions 12,14 may alternatively be juxtaposing portions. Sag is calculated as the ratio of the measurement at the bottom portion 14 ($m_b$ or $\rho_b$) to the sum of the measurements of the bottom portion 14 and the top portion 12 ($m_t$ or $\rho_t$), as outlined in Equations 1 and 2.

$$\text{sag} = \frac{m_b}{[m_b + m_t]} \quad \text{Equation 1}$$

$$\text{sag} = \frac{\rho_b}{[\rho_b + \rho_t]} \quad \text{Equation 2}$$

Generally for weighting agents used in wellbore operations, a fluid with a sag less than 0.5 is conserved to be non-sagging, while sag greater than about 0.52 may potentially have operations issues downhole (e.g., cause stuck pipes, kicks, loss circulation, etc.). As will be appreciated, the sag depends on the location of the two measurement points relative to each other. One skilled in the art would be able to readily determine appropriate locations or distance difference in locations based on the fluid composition and sag characteristics suitable for the fluid relative to the use of the fluid. For example, when analyzing a fluid for use in deviated wellbores, the distance between the locations may be smaller than in vertical wellbore applications.

However, understanding the sag of other particles like lost circulation materials and proppants in wellbore fluids is of value. For example, analyzing sag of a proppant slurry may provide an indication of the carrying capacity of the slurry and allow for maximizing the amount of proppant placed downhole in a fracturing and propping operation.

Without being limited by theory, it is believed that the thermal conductivity of a fluid is inversely proportional to the mass or density of particles in a fluid. As described above, sag relates to particulate settling that creates an inhomogeneous fluid composition. Therefore, measuring the thermal conductivity of the fluid at two or more locations in the fluid may provide an indication of the particle mass or density at the points of measurement, which may be used to extrapolate the sag in the fluid. Such extrapolation may utilize a known relationship between thermal conductivity and particle mass or density for a given base fluid and particle composition. Further, the relationship may take into account the base fluid as different base fluids have different thermal conductivities. This relationship may be measured experimentally on site or provided based on experimental data. For example, barite and calcium carbonate mixtures in various relative concentrations and various total concentrations may be used to calibrate for density relative to thermal conductivity.

Therefore, in addition to more straightforward and, optionally, automated methods for measuring weighting agent sag, the methods and apparatuses described herein may be useful in measuring sag of other particles like lost circulation materials and proppants.

Figure 2:
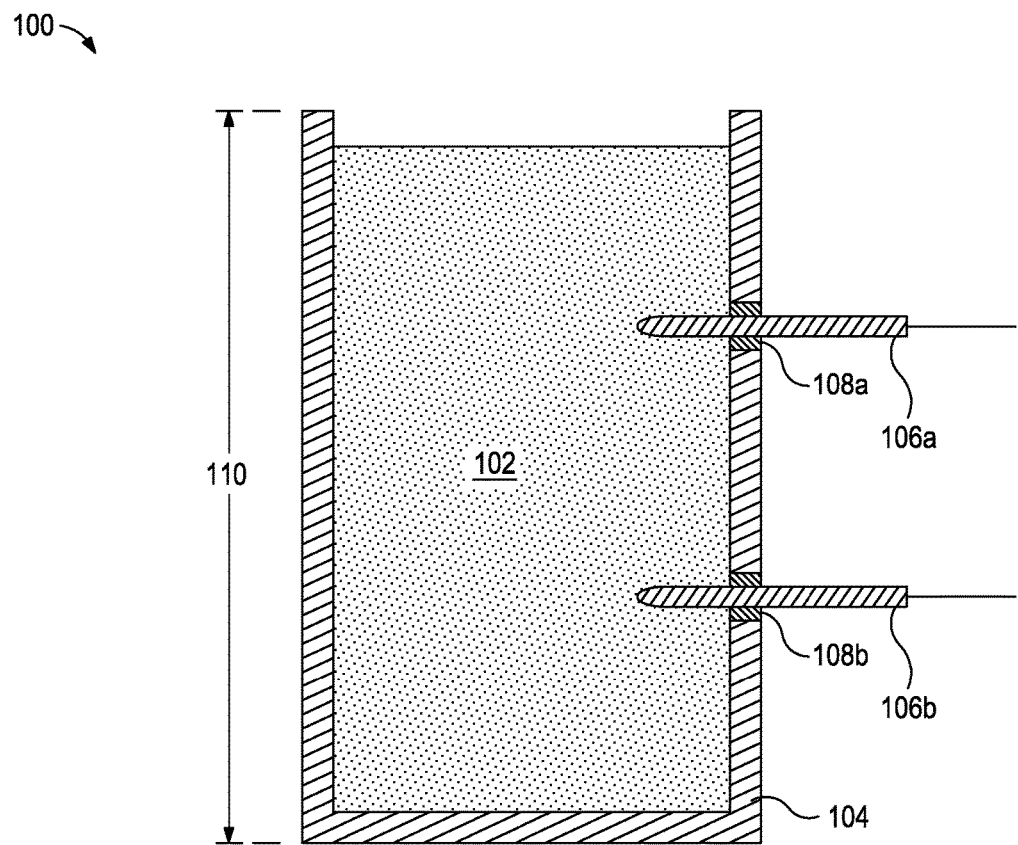
FIG. 2 provides a cross-sectional diagram of a portion of an apparatus for measuring the thermal conductivity and extrapolating the sag of the fluid.

FIG. 2 provides a cross-sectional diagram of a portion of an apparatus 100 for measuring the thermal conductivity and extrapolating the sag of the fluid 102. The apparatus 100 includes a vessel 104 configured to containing a fluid 102. The apparatus 100 also includes two thermal conductivity sensors 106a,106b configured to measure the thermal conductivity of the fluid 102 at two locations along the height 110 of the vessel 104. While the apparatus 100 is illustrated to include two thermal conductivity sensors 106a,106b, other configurations may be suitable with any number of thermal conductivity sensors (e.g., 1 to 20).

As illustrated, the thermal conductivity sensors 106a, 106b are probes that extend through ports 108a,108b, respectively, in the vessel 104. This apparatus 100 and similar configurations may be useful in measuring thermal conductivity and extrapolating static sag of the fluid 102 (i.e., sag under static conditions). In some instances, the illustrated configuration may allow for measuring sag of the fluid over time. For example, the thermal conductivity may be measured every few minutes at each location and recorded, which provides a time basis for particle migration (or sag) that can be used to calculate settling velocity.

Figure 3:
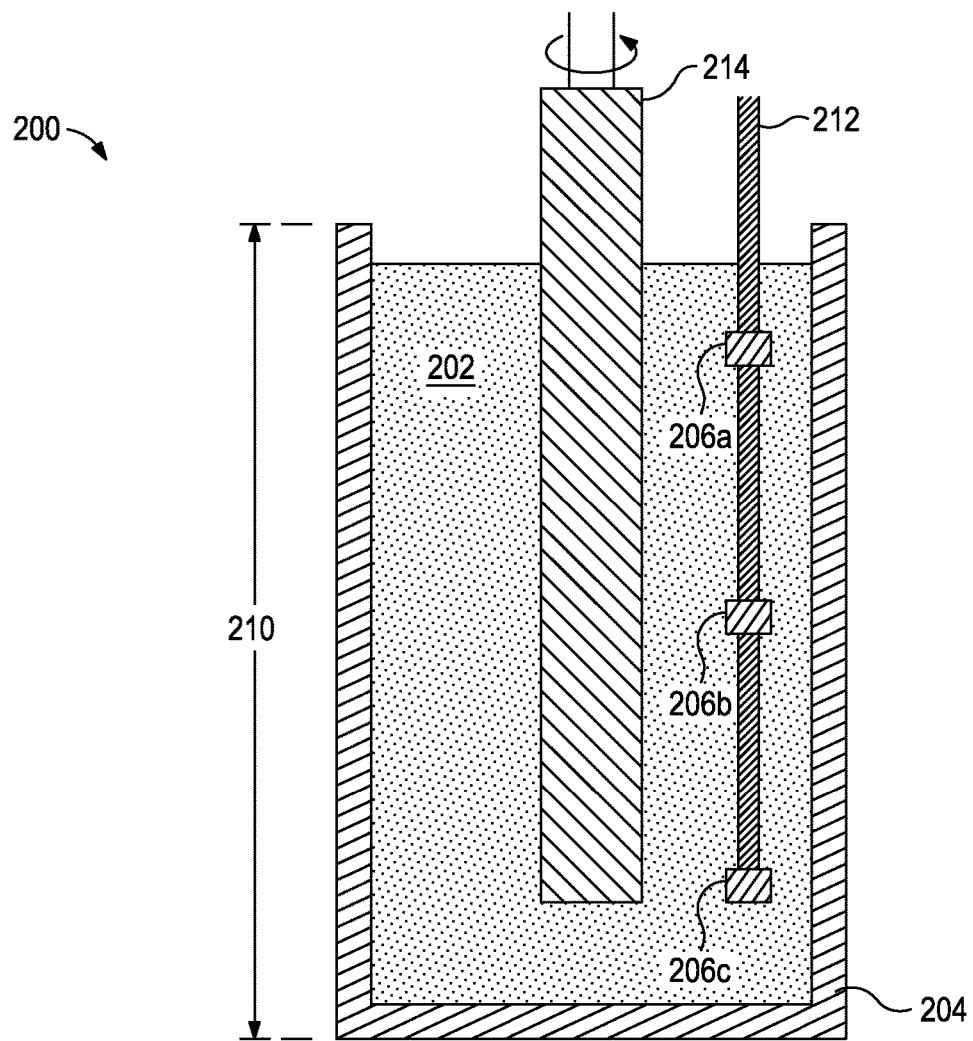
FIG. 3 provides a cross-sectional diagram of a portion of an apparatus for measuring the thermal conductivity and extrapolating the sag of a fluid.

FIG. 3 provides a cross-sectional diagram of a portion of an apparatus 200 for measuring the thermal conductivity and extrapolating the sag of a fluid 202. The apparatus 200 includes a vessel 204 configured for containing the fluid 202 and three thermal conductivity sensors 206a,206b,206c configured to measure the thermal conductivity of the fluid 202 at three locations along the height 210 of the vessel 204. As illustrated, the thermal conductivity sensors 206a,206b,206c are disposed on a rod 212 that is inserted into the fluid 202 through the top of the vessel 204. In some configurations, sensors 206a,206b,206c may alternatively be mechanically placed at various positions in the fluid as required.

The apparatus 200 also includes a bob 214 that extends through the top of the vessel 204 and into the fluid 202. The bob 214 and vessel 204 may be configured to rotate relative to each other. As illustrated, the bob 214 rotates and the vessel 204 is stationary. However, in alternate embodiments, both may rotate or the bob 214 may be stationary with a rotating vessel 204. This relative rotation allows for shearing the fluid 202 while measuring the thermal conductivity for extrapolating dynamic sag of the fluid 202 (i.e., sag under shearing conditions).

Figure 4:
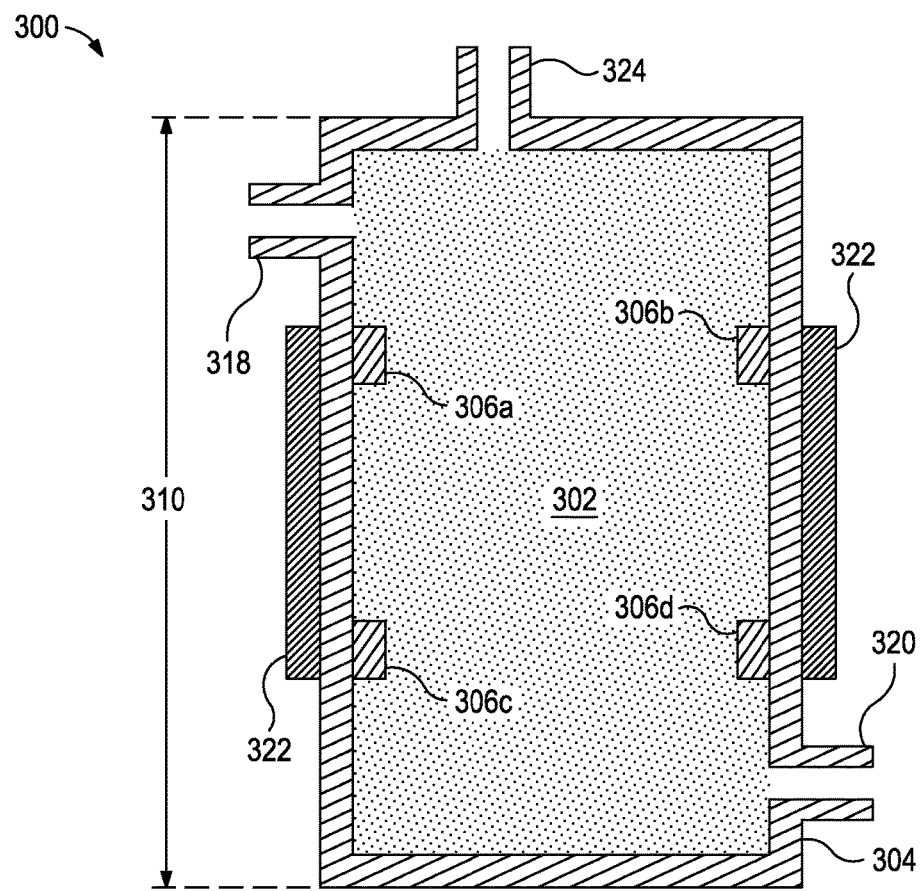
FIG. 4 provides a cross-sectional diagram of a portion of an apparatus for measuring the thermal conductivity and extrapolating the sag of a fluid.

FIG. 4 provides a cross-sectional diagram of a portion of an apparatus 300 for measuring the thermal conductivity and extrapolating the sag of a fluid 302. The apparatus 300 includes a vessel 304 configured for containing the fluid 302 and four thermal conductivity sensors 306a,306b,306c, 306d. As illustrated, the thermal conductivity sensors 306a, 306b,306c,306d are disposed on the inside of the vessel 304 as two pairs of sensors 306a,306b and 306c,306d with each pair at a different location along the height 310 of the vessel 304. Each sensor in the pair is positioned opposite the other in the vessel 304. Such configurations may allow for averaging the thermal conductivity measurements at the designated location along the height 310 of the vessel 304 for increased accuracy.

The vessel 304 includes a fluid inlet 318 and a fluid outlet 320 for transferring the fluid 302 and any cleaning or flushing fluids into and out of the vessel 320. This vessel configuration provides for sag analysis capabilities in-line with a larger system (e.g., a drilling assembly or other well site assembly).

The apparatus 300 also includes a thermal device 322 coupled to the vessel 304 for increasing or decreasing the temperature of the fluid 302. While the thermal device 322 is depicted as directly coupled to the vessel 304, in alternate embodiments, the thermal device 322 may be in thermal communication with the vessel 304 without direct coupling or touching. The thermal device 322 may be used in methods where the temperature of the fluid 302 is adjusted for the thermal conductivity measurements.

The apparatus 300 further includes a pressure port 324 that may be coupled to a pump (not illustrated) for adjusting the pressure applied to the fluid 302 in the vessel 304. The pump may be used in methods where the pressure applied to the fluid 302 is adjusted for the thermal conductivity measurements.

One skilled in the art would recognize the additional components that may be required for proper operation of the apparatus 300. For example, valves and fluid handling components may be included for transferring the fluid 302 into and out of the vessel 304 and for cleaning the vessel 304. Additionally, valves may be included to appropriately seal the vessel when the pressure therein is increased. Further, insulation may be included for more efficient temperature maintenance when using the thermal device 322.

In some instances, hybrids of the foregoing apparatuses 100,200,300 may be used for measuring thermal conductivity of a fluid for extrapolating sag of the fluid. For example, the apparatus 200 of FIG. 3 may further include a thermal device.

In some embodiments, a system may include one or more apparatuses described herein for measuring thermal conductivity of a fluid at various locations along the height of a vessel containing the fluid, which may be referred to herein as "thermal conductivity measurement apparatuses" for short.

Figure 5:
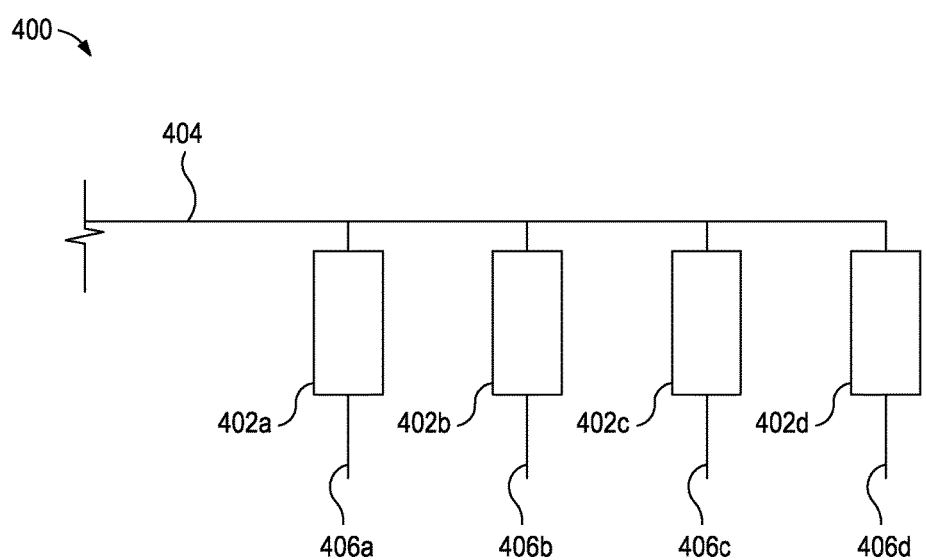
FIG. 5 illustrates a portion of a system that includes multiple thermal conductivity measurement apparatuses FIG. 6 provides a diagram of a wellbore drilling assembly, according to one or more embodiments, that includes one or more thermal conductivity measurement apparatuses.

FIG. 5 illustrates a portion of a system 400 that includes multiple thermal conductivity measurement apparatuses 402a,402b,402c,402d. While the portion of the system 400 is illustrated to include four thermal conductivity measurement apparatuses 402a,402b,402c,402d, other configurations may be suitable with any number of apparatuses (e.g., 1 to 20).

Figure 6:
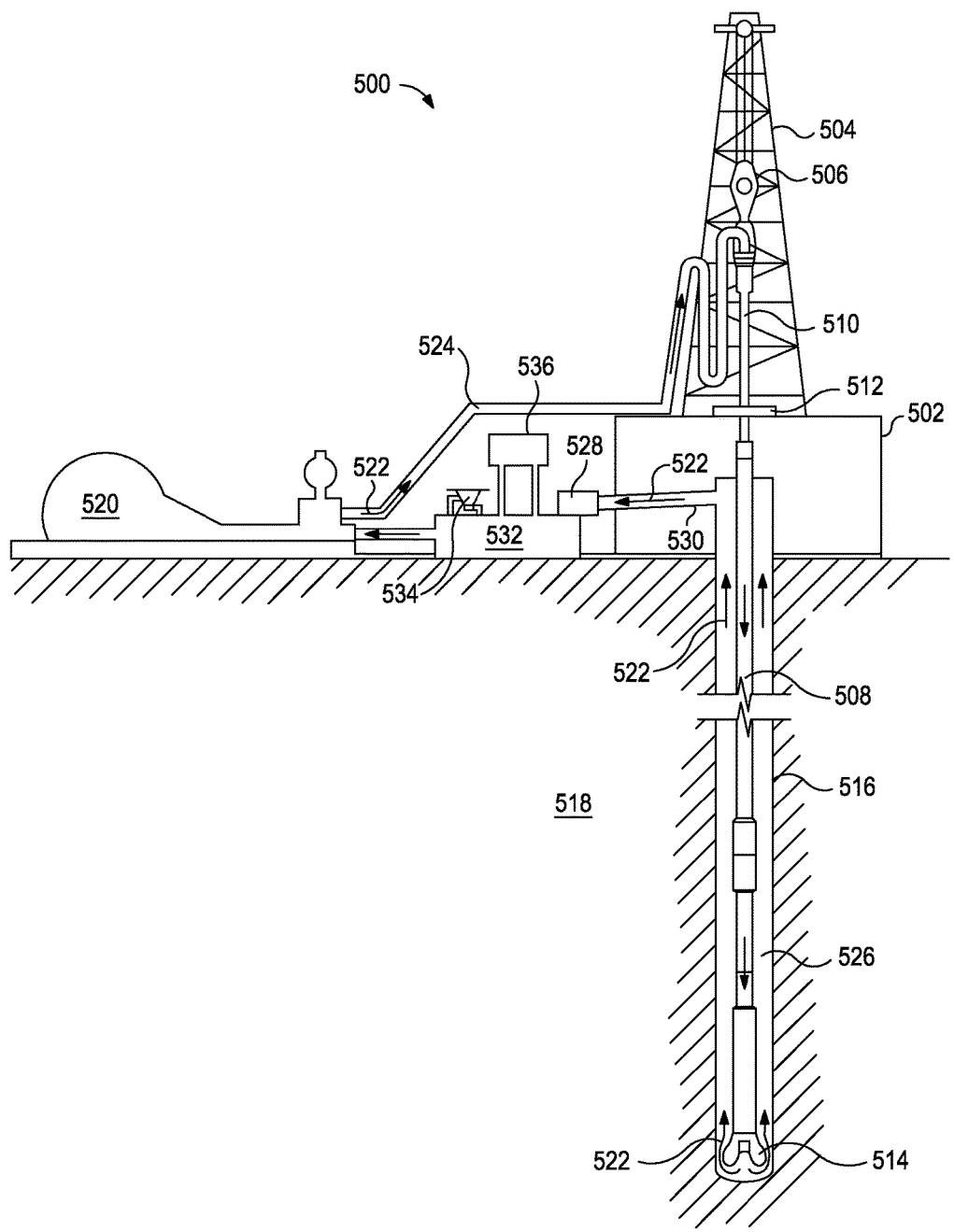

The illustrated portion of the system 500 includes a flow line 504 extending from another portion of the system (e.g., a retention pit 532 illustrated in FIG. 6). The flow line 404 is fluidly coupled each of the thermal conductivity measurement apparatuses 402a,402b,402c,402d for delivering fluid from the other portion of the system to the thermal conductivity measurement apparatuses 402a,402b,402c,402d. Each of the thermal conductivity measurement apparatuses 502a, 502b,502c,502d also include fluid outlet lines 406a,406b, 406c,406d for flowing the fluid out of the thermal conductivity measurement apparatuses 402a,402b,402c,402d after the prescribed measurements and/or cleaning the thermal conductivity measurement apparatuses 402a,402b,402c, 402d.

Each of the thermal conductivity measurement apparatuses 402a,402b,402c,402d may be configured differently or the same. For example, each may be configured similar to the apparatus 100 of FIG. 2. Alternatively, each may be configured differently as a variation of the apparatus 100 of FIG. 2 (e.g., one being configured for heating the sample, one being configured for pressurizing the sample, one being configured for dynamic measurements, and one being configured for static measurements).

In some instances, the conditions experienced by the fluid in each of the thermal conductivity measurement apparatuses 402a,402b,402c,402d may be different, whether the thermal conductivity measurement apparatuses 402a,402b, 402c,402d are configured the same or differently. For example, each of the thermal conductivity measurement apparatuses 402a,402b,402c,402d may have heating and shearing capabilities but the fluid samples may be analyzed at different temperatures and/or shear rates.

FIG. 6, for example, provides a diagram of a wellbore drilling assembly 500, according to one or more embodiments, that includes one or more thermal conductivity measurement apparatuses 536. It should be noted that while FIG. 6 generally depicts a land-based drilling assembly, those skilled in the art will readily recognize that the principles described herein are equally applicable to subsea drilling operations that employ floating or sea-based platforms and rigs, without departing from the scope of the disclosure.

As illustrated, the drilling assembly 500 may include a drilling platform 502 that supports a derrick 504 having a traveling block 506 for raising and lowering a drill string 508. The drill string 508 may include, but is not limited to, drill pipe and coiled tubing, as generally known to those skilled in the art. A kelly 510 supports the drill string 508 as it is lowered through a rotary table 512. A drill bit 514 is attached to the distal end of the drill string 508 and is driven either by a downhole motor and/or via rotation of the drill string 508 from the well surface. As the bit 514 rotates, it creates a wellbore 516 that penetrates various subterranean formations 518.

A pump 520 (e.g., a mud pump) circulates drilling fluid 522 through a feed pipe 524 and to the kelly 510, which conveys the drilling fluid 522 downhole through the interior of the drill string 508 and through one or more orifices in the drill bit 514. The drilling fluid 522 is then circulated back to the surface via an annulus 526 defined between the drill string 508 and the walls of the wellbore 516. At the surface, the recirculated or spent drilling fluid 522 exits the annulus 526 and may be conveyed to one or more fluid processing unit(s) 528 via an interconnecting flow line 530. After passing through the fluid processing unit(s) 528, a "cleaned" drilling fluid 522 is deposited into a nearby retention pit 532 (i.e., a mud pit). While illustrated as being arranged at the outlet of the wellbore 516 via the annulus 526, those skilled in the art will readily appreciate that the fluid processing unit(s) 528 may be arranged at any other location in the drilling assembly 500 to facilitate its proper function, without departing from the scope of the scope of the disclosure.

One or more additives (e.g., weighting agents) may be added to the drilling fluid 522 via a mixing hopper 534 communicably coupled to or otherwise in fluid communication with the retention pit 532. The mixing hopper 534 may include, but is not limited to, mixers and related mixing equipment known to those skilled in the art. In other embodiments, however, additives may be added to the drilling fluid 522 at any other location in the drilling assembly 500. In at least one embodiment, for example, there could be more than one retention pit 532, such as multiple retention pits 532 in series. Moreover, the retention pit 532 may be representative of one or more fluid storage facilities and/or units where additives may be stored, reconditioned, and/or regulated until added to the drilling fluid 522.

The drilling assembly 500 may include one or more thermal conductivity measurement apparatuses 536 in fluid communication with the at least one retention pit 532. Samples of the drilling fluid in the retention pits 532 may be transported to the thermal conductivity measurement apparatuses 536 to measure the sag of the drilling fluid 522.

While not specifically illustrated herein, the drilling assembly 500 may also include additional components, for example, shakers (e.g., shale shaker), centrifuges, hydrocyclones, separators (e.g., magnetic and electrical separators), desilters, desanders, filters (e.g., diatomaceous earth filters), heat exchangers, fluid reclamation equipment, sensors, gauges, pumps, compressors, conduits, pipelines, trucks, tubulars, pipes, pumps, compressors, motors, valves, floats, drill collars, mud motors, downhole motors, downhole pumps, MWD/LWD tools, tool seals, packers, roller cone bits, PDC bits, natural diamond bits, any hole openers, reamers, coring bits, and the like, and any communication components associated therewith (e.g., wirelines, telemetry components, etc.).

Figure 7:
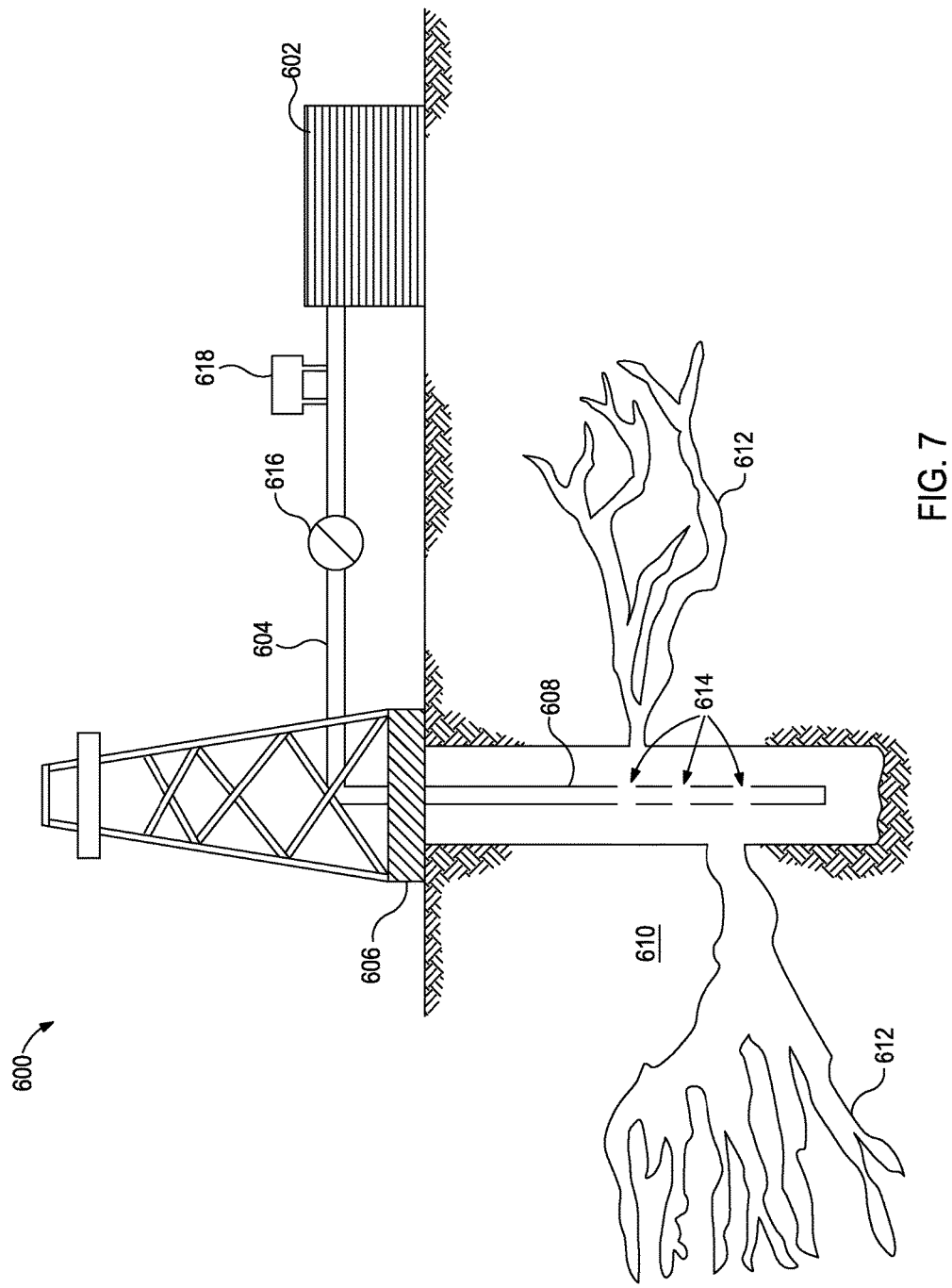
FIG. 7 provides an illustrative schematic of a system for delivering a proppant slurry to a downhole location, according to one or more embodiments.

In another system example, sag may be useful in analyzing the carrying capacity of a proppant slurry. FIG. 7 provides an illustrative schematic of a system 600 for delivering a proppant slurry to a downhole location, according to one or more embodiments. It should be noted that while FIG. 7 generally depicts a land-based system, it is to be recognized that like systems may be operated in subsea locations.

The system 600 includes mixing tank 602, in which a proppant and base fluid may be mixed to form the proppant slurry. The proppant slurry may be conveyed via line 604 to wellhead 606, where the proppant slurry enters tubular 608 that extends from wellhead 606 into subterranean formation 610. Upon being ejected from tubular 608, the proppant slurry may subsequently exit the tubular 608 via the orifices 614 and penetrate into fractures 612 in the subterranean formation 18 to form a proppant pack therein. In some instances, the wellbore may further comprise equipment or tools (not shown) for zonal isolation of a portion of the subterranean formation 18 to be treated.

Pump 616 may be configured to raise the pressure of the proppant slurry to a desired degree before its introduction into tubular 608. Upstream of the pump 616 or on the low-pressure side of the pump 616, one or more thermal conductivity measurement apparatuses 618 may be coupled to the line 604. Portions of the proppant slurry being transported from the mixer 602 to the wellhead 606 may be sampled and transported to the thermal conductivity measurement apparatuses 618 for analysis. Based on the amount of sag in the proppant slurry, the concentrations of base fluid and proppant in the proppant slurry may be adjusted to maximize the amount of proppant being delivered downhole without significantly exceeding the carrying capacity of the proppant slurry.

In the foregoing systems or similar systems with in-line thermal conductivity measurement apparatuses, the sag analysis of the fluid may be useful in determining or adjusting operational parameters of the corresponding wellbore operation. Exemplary operational parameters may include, but are not limited to, pump-off time, flow rate downhole, composition of the wellbore fluid, pipe rpm, tripping speeds, surface cleaning equipment operating parameters, and the like, and any combination thereof. For example, fluids that exhibit sag may have increased fluid flow rates to mitigate sag. In another example, the composition of the fluid may be changed so as to decrease the concentration of particles or increase the concentration of viscosifier to reduce sag. In yet another example, where manipulating the fluid composition may require more time than available, a choke may be used to manage wellbore pressure where sag may be occurring.

In some instances, the foregoing systems or similar systems with in-line thermal conductivity measurement apparatuses may be automated such that the sag analysis is performed periodically and the results are transmitted to a processor (e.g., a computer) that includes a mathematical model that uses the fluid's sag to determine or predict operational parameters. In some instances, such operational parameters may be adjusted automatically or by an operator based on the determined or predicted operational parameters that include the sag analysis from the thermal conductivity measurements.

In addition to wellbore operations, sag may be encountered in the storage and transport of fluids having particles dispersed therein. When fluids sag during storage or transport, they may need to be remixed before use. The methods described herein may be useful in measuring the sag of fluids during transport or storage so that appropriate remedial action may be taken to homogenize the fluid having particles dispersed therein. As such, the vessel of the foregoing illustrations (e.g., vessels 104,204,304 of FIGS. 1-3) may be replaced with an appropriately configured transport or storage vessel. For example, when transporting drums of particle-laden fluid, one or more of the drums may have two or more thermal conductivity sensors therein. Once at the site for use, the sag of the fluid therein may be extrapolated from the thermal conductivity measurements. For sagging fluids, the particle-laden fluid may be mixed in the drums (e.g., by inversion or rolling of the drums or with a paddle or similar mixing devices). This may provide a fluid that pours more easily from the drums without leaving significant amounts of particles at the bottom of the drum. Additionally, if no sag is observed, unnecessary procedures for agitating the drums may be avoided. This concept may similarly be extended to larger tanker vessels where pumps are used to transport the particle-laden fluid to another location. When the fluid sags, the pump pressure or force needed to transport the portion with more particles increases. So appropriate mixing may reduce pump energy requirements and peak system pressures that the more viscous sagging material would manifest.

Embodiments disclosed herein include Embodiment A, Embodiment B, and Embodiment C.

Embodiment A: A method involving measuring a thermal conductivity of a fluid at two or more locations along a height of a vessel containing the fluid that comprises particles dispersed in a base fluid; and calculating a sag of the fluid based on the thermal conductivity at the two or more locations.

Embodiment A may have one or more of the following additional elements in any combination: Element 1: the method further including applying shear to the wellbore fluid while measuring the thermal conductivity; Element 2: the method further including increasing a temperature of the wellbore fluid contained in the vessel before measuring the thermal conductivity; Element 3: the method further including increasing a pressure in the vessel before measuring the thermal conductivity; Element 4: wherein the fluid is a wellbore fluid and the method further comprises: adjusting an operational parameter of a wellbore operation using the wellbore fluid based on the sag of the wellbore fluid; Element 5: Element 4 wherein the wellbore fluid is a drilling fluid and the particles include a weighting agent; Element 6: Element 4 wherein the wellbore fluid is a drilling fluid and the particles include a lost circulation material; Element 7: Element 4 wherein the wellbore fluid is a proppant slurry and the particles include a proppant; Element 8: Element 4 wherein the operational parameter is a pump-off time; Element 9: Element 4 wherein the operational parameter is a wellbore fluid flow rate downhole; Element 10: Element 4 wherein the operational parameter is a composition of the wellbore fluid; Element 11: wherein the fluid is a drilling fluid and the method further comprises: transporting the drilling fluid from a mud pit at a well site to the vessel; Element 12: wherein the fluid is a sample of a proppant slurry and the method further comprises: mixing a base fluid and a proppant to form the proppant slurry; and extracting the sample from the proppant slurry before pressurizing the proppant slurry for placement downhole; Element 13: wherein the vessel is a first vessel and the method further involves: measuring the thermal conductivity of the wellbore fluid as a function of time at two or more locations along a height of a second vessel containing the wellbore fluid, wherein a condition of the drilling fluid contained in the first and second vessels, a geometry of the first and second vessels, or both are different; calculating a sag rate of the wellbore fluid based on the thermal conductivity as a function of time at the two or more locations in the first vessel and the second vessel; and adjusting an operational parameter of a wellbore operation using the wellbore fluid based on the sag rate of the wellbore fluid; Element 14: Element 13 and wherein the condition of the drilling fluid is a temperature of the drilling fluid, a pressure applied to the drilling fluid, or both; and Element 15: Element 13 and wherein the condition of the drilling fluid is a shear rate applied to the drilling fluid.

By way of non-limiting example, exemplary combinations applicable to Embodiment A include: at least two of Elements 1-3 in combination, at least one of Elements 1-3 in combination with Element 4 and at least one of Elements 5-6 or Element 7; Elements 4-6 in combination and optionally in further combination with Element 11; Elements 4, 7, and 12 in combination; Element 4 in combination with at least one of Elements 8-10 and either at least one of Elements 5-6 or Element 7; Element 4 in combination with at least two of Elements 8-10; Element 13 in combination with any of the foregoing; Element 13 and at least one of Elements 14-15 in combination with at least one of Elements 4-6 and optionally in further combination with Element 11; and so on.

Embodiment B: A system having a drilling platform operably coupled to a drill string extending into a wellbore; a drill bit attached to the distal end of the drill string; a pump operably connected to the drill string for circulating the drilling fluid through the drill string to an annulus defined by the drill string and the wellbore to a fluid processing unit and to a retention pit; and one or more thermal conductivity measurement apparatuses in fluid communication with the retention pit, the one or more thermal conductivity measurement apparatuses comprising: a vessel with two or more thermal conductivity sensors disposed therein and located within the vessel at two or more locations along a height of a vessel.

Embodiment C: A system having a line fluidly connecting a mixing tank and a tubular extending into a wellbore with a pump disposed along the line between the mixing tank and the tubular; and one or more thermal conductivity measurement apparatuses in fluid communication with the line between the mixing tank and the pump, the one or more thermal conductivity measurement apparatuses comprising: a vessel with two or more thermal conductivity sensors disposed therein and located within the vessel at two or more locations along a height of a vessel.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

One or more illustrative embodiments incorporating the invention embodiments disclosed herein are presented herein. Not all features of a physical implementation are described or shown in this application for the sake of clarity. It is understood that in the development of a physical embodiment incorporating the embodiments of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill the art and having benefit of this disclosure.

While compositions and methods are described herein in terms of "comprising" various components or steps, the compositions and methods can also "consist essentially of" or "consist of" the various components and steps.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

The invention claimed is:

1. A method comprising:
  measuring a first thermal conductivity of a fluid at a first location along a height of a vessel containing the fluid that comprises particles dispersed in a base fluid;
  measuring a second thermal conductivity of the fluid at a second location along the height of the vessel; and
  calculating a sag of the fluid based on (1) a ratio of either a first or a second density of the fluid over a sum of the first and second densities, wherein the first and second densities are determined based on the measured first and second thermal conductivities, respectively; or (2) a ratio of either a first or a second mass of the particles in the fluid over a sum of the first and second masses, wherein the first and second masses are determined based on the measured first and second thermal conductivities, respectively.

2. The method of claim 1 further comprising:
  applying shear to the fluid while measuring at least one of the first or the second thermal conductivity.

3. The method of claim 1 further comprising:
  increasing a temperature of the fluid contained in the vessel before measuring at least one of the first or the second thermal conductivity.

4. The method of claim 1 further comprising:
  increasing a pressure in the vessel before measuring at least one of the first or the second thermal conductivity.

5. The method of claim 1, wherein the fluid is a wellbore fluid and the method further comprises: adjusting an operational parameter of a wellbore operation using the wellbore fluid based on the sag of the wellbore fluid.

6. The method of claim 5, wherein the wellbore fluid is a drilling fluid and the particles include a weighting agent.

7. The method of claim 5, wherein the wellbore fluid is a drilling fluid and the particles include a lost circulation material.

8. The method of claim 5, wherein the wellbore fluid is a proppant slurry and the particles include a proppant.

9. The method of claim 5, wherein the operational parameter is a pump-off time.

10. The method of claim 5, wherein the operational parameter is a wellbore fluid flow rate downhole.

11. The method of claim 5, wherein the operational parameter is a composition of the wellbore fluid.

12. The method of claim 1, wherein the fluid is a drilling fluid and the method further comprises: transporting the drilling fluid from a mud pit at a well site to the vessel.

13. The method of claim 1, wherein the fluid is a sample of a proppant slurry and the method further comprises: mixing a base fluid and a proppant to form the proppant slurry; and extracting the sample from the proppant slurry before pressurizing the proppant slurry for placement downhole.

14. A method comprising:
measuring a thermal conductivity of a drilling fluid as a function of time at two or more locations along a height of a first vessel containing the drilling fluid that comprises particles dispersed in the drilling fluid;
measuring a thermal conductivity of the drilling fluid as a function of time at two or more locations along a height of a second vessel containing the drilling fluid, wherein a condition of the drilling fluid contained in the first and second vessels, a geometry of the first and second vessels, or both are different;
calculating a sag rate of the drilling fluid based on the thermal conductivity as a function of time at the two or more locations in the first vessel and the second vessel; and
adjusting an operational parameter of a wellbore operation using the wellbore fluid based on the sag rate of the drilling fluid.

15. The method of claim 14, wherein the condition of the drilling fluid is a temperature of the drilling fluid, a pressure applied to the drilling fluid, or both.

16. The method of claim 14, wherein the condition of the drilling fluid is a shear rate applied to the drilling fluid.

17. A system comprising:
a drilling platform operably coupled to a drill string extending into a wellbore;
a drill bit attached to the distal end of the drill string;
a pump operably connected to the drill string for circulating a drilling fluid through the drill string to an annulus defined by the drill string and the wellbore to a fluid processing unit and to a retention pit; and
one or more thermal conductivity measurement apparatuses in fluid communication with the retention pit, the one or more thermal conductivity measurement apparatuses comprising: a first vessel with two or more thermal conductivity sensors disposed therein and located within the first vessel at two or more locations along a height of the first vessel, and a second vessel with two or more thermal conductivity sensors disposed therein and located within the second vessel at two or more locations along a height of the second vessel, wherein a condition of the drilling fluid contained in the first and second vessels, a geometry of the first and second vessels, or both are different.

18. A system comprising:
a line fluidly connecting a mixing tank and a tubular extending into a wellbore with a pump disposed along the line between the mixing tank and the tubular;
one or more thermal conductivity measurement apparatuses in fluid communication with the line between the mixing tank and the pump, the one or more thermal conductivity measurement apparatuses comprising: a first vessel with two or more thermal conductivity sensors disposed therein and located within the first vessel at two or more locations along a height of the first vessel, and a second vessel with two or more thermal conductivity sensors disposed therein and located within the second vessel at two or more locations along a height of the second vessel, wherein a condition of a drilling fluid contained in the first and second vessels, a geometry of the first and second vessels, or both are different.

* * * * *